US009763640B2

(12) United States Patent
Li et al.

(10) Patent No.: US 9,763,640 B2
(45) Date of Patent: Sep. 19, 2017

(54) 3D IMAGE GENERATION METHOD AND DEVICE FOR G-ARM X-RAY MACHINE AND G-ARM X-RAY MACHINE

(75) Inventors: Fubing Li, Beijing (CN); Shiyu Wei, Beijing (CN); Xun Zhu, Beijing (CN)

(73) Assignee: BEIJING EAST WHALE IMAGE TECHNOLOGY CO., LTD., Beijing (CN)

( * ) Notice: Subject to any disclaimer, the term of this patent is extended or adjusted under 35 U.S.C. 154(b) by 317 days.

(21) Appl. No.: 14/411,392

(22) PCT Filed: Jun. 29, 2012

(86) PCT No.: PCT/CN2012/077933
§ 371 (c)(1),
(2), (4) Date: Dec. 25, 2014

(87) PCT Pub. No.: WO2014/000279
PCT Pub. Date: Jan. 3, 2014

(65) Prior Publication Data
US 2015/0190108 A1    Jul. 9, 2015

(51) Int. Cl.
*A61B 6/00* (2006.01)
*G06T 11/00* (2006.01)
*A61B 6/02* (2006.01)

(52) U.S. Cl.
CPC .............. *A61B 6/582* (2013.01); *A61B 6/022* (2013.01); *A61B 6/4014* (2013.01);
(Continued)

(58) Field of Classification Search
CPC ..... A61B 6/022; A61B 6/4014; A61B 6/4085; A61B 6/4441; A61B 6/4476; A61B 6/52;
(Continued)

(56) References Cited

U.S. PATENT DOCUMENTS 5,367,554 A * 11/1994 Kobayashi ............... A61B 6/00
378/196
2006/0262893 A1 * 11/2006 Tang ..................... G06T 11/006
378/4

(Continued)

FOREIGN PATENT DOCUMENTS

CN    201572102 U    9/2010
CN    102715914 A    10/2012

OTHER PUBLICATIONS

International Search Report for PCT/CN2012/077933.
(Continued)

*Primary Examiner* — Irakli Kiknadze
(74) *Attorney, Agent, or Firm* — The PL Law Group, PLLC

(57) ABSTRACT

A 3D image generation method includes controlling a G-arm frame to rotate to a target angle, and keeping the currents and voltages of two X-ray tubes unchanged during rotation, obtaining groups of 2D projection data of an object when a G-arm is in different angles, each group of 2D projection data including two paths of projection data, conducting calculation according to an FDK algorithm or an FDK correction algorithm using the groups of 2D projection data to obtain a 3D image of the object, and outputting the 3D image, thereby greatly reducing the data obtaining time by obtaining two paths of projection data, effectively reducing the irradiation time of the object, directly outputting the 3D image of the object, reflecting the full view information about the object, and solving the problem in the prior art that the irradiation time of the object under examination of X-rays is long.

13 Claims, 5 Drawing Sheets

(52) U.S. Cl.
CPC .......... *A61B 6/4085* (2013.01); *A61B 6/4441* (2013.01); *A61B 6/4476* (2013.01); *A61B 6/52* (2013.01); *G06T 11/006* (2013.01); *G06T 2211/421* (2013.01)

(58) Field of Classification Search
CPC ......... A61B 6/582; A61B 6/032; A61B 6/035; A61B 6/06; A61B 6/4452; A61B 6/02; A61B 6/4021; A61B 6/4233; A61B 6/56; A61B 6/4447; A61B 6/4411; A61B 6/4429; A61B 6/4435; A61B 6/4464; A61B 6/027; A61B 6/583; A61B 6/5205; A61B 6/5258; A61B 6/14; A61B 6/484; A61B 6/5264; A61B 6/4291; A61B 6/5282; A61B 6/5288; A61B 6/587; A61B 6/4028; G06T 11/006; G06T 2211/421; G06T 11/005
USPC ............................ 378/4, 9, 62; 382/131, 132
See application file for complete search history.

(56) References Cited

U.S. PATENT DOCUMENTS

2007/0297661 A1* 12/2007 Zhu ..................... G06T 11/006
382/131
2012/0301004 A1* 11/2012 Kingston ............... A61B 6/032
382/131

OTHER PUBLICATIONS

Zhang et al., Review of recent development in FDK reconstruction algorithms for 3D cone beam CT, Chinese Journal of Stereology and Mage Analysis vol. 10, No. 2, pp. 116-121, Jun. 2005.

* cited by examiner

3D IMAGE GENERATION METHOD AND DEVICE FOR G-ARM X-RAY MACHINE AND G-ARM X-RAY MACHINE

TECHNICAL FIELD

The present invention relates to the field of medical instrument, and more specifically, to a 3D image generation method and device for a G-arm X-ray machine as well as a G-arm X-ray machine.

BACKGROUND ART

At present, imaging from an X-ray machine is generally provided in the form of 2D images, and currently available solutions include Computed Tomography (CT), C-arm Perspective Image, etc. However, 2D image information is only image data of a certain angle or a certain section, which cannot reflect the full view information of the imaging portion.

In recent years, techniques of constructing 3D images using 2D projection images come into being, mainly including:

The Computed Tomography, which comprises using parallel or sectional X-rays to perform ray projection measurement from different angles for the section of the object under detection to obtain 360° ray projection data; performing counter-projection calculation on the ray projection data to obtain a reconstructed image of the 2D slice; then piecing together the continuously obtained 2D slice image data to obtain the 3D reconstructed image data of the target, so that tomography scanning can be carried out using CT, and analysis is conducted in the manner of images. However, the parallel or sectional ray mechanism of CT results in a low light field utilization rate of the X-ray tube.

The Cone Beam Computed Tomography (CBCT), which comprises performing ray perspective projection of the object using a cone-shape stereoscopic beam ray source and an array detector, so that the projection data of a plurality of sections of the object under detection can be obtained by only one scanning. The 3D image of the target can be reconstructed by a series of perspective projections from different angles according to respective reconstruction algorithms. Compared to traditional CT planar ray beam, CBCT is advantageous for its high ray utilization rate and being capable of reconstructing the 3D image. Traditional C-arm X-ray machines nearly meet the application requirements of CBCT, so the CBCT technique has been conveniently applied to C-arm X-ray machines. The process of CBCT scanning using a C-arm X-ray machine desires that the X-ray tube of the C-arm at least rotates 180°+2γ around the detection target, wherein γ is the half angle of the X-ray beam of the CBCT, and then 3D reconstruction is carried out by multi-angle 2D projections.

For the algorithm bases of reconstructing a 3D image based on 2D projection image data, please refer to L. A. Feldkamp, L. C. Davis and J. W. Kress. Practical cone-beam algorithm, J. Opt. Soc. Am. A, vol. 1, no. 6, 1984, pp. 612-619. Such an FDK algorithm is a classical appropriate 3D image reconstruction algorithm, which has a simple mathematical form and can be easily carried out, and moreover, in case of a relatively small cone angle, can achieve a good reconstruction effect, so it has been widely used. In order to adapt to practical conditions for measurement of the C-arm, K. Wiesent made corresponding improvements on the FDK algorithm. Please refer to K. Wiesent, K. Barth, N. Navab, et al. Enhanced 3-D reconstruction algorithm for C-Arm systems suitable for interventional procedures. IEEE Trans. Med. Imag., vol. 19, no. 5, 2000, pp. 391-403.

However, said method for reconstructing a 3D image by a C-arm X-ray machine using CBCT has the following problems:

1. The process of CBCT scanning using a C-arm X-ray machine desires that the X-ray tube of the C-arm at least rotates 180°+2γ around the detection target, and the image is obtained in a long time period, so that the target under detection is radiated under the X-ray for a long time, resulting in a low measurement efficiency.

2. CBCT has an uneven spatial light field intensity distribution, because the light field intensity of the center ray beam of the X-ray beam is greater than the light field intensity at other positions, and such inconsistency in light field intensity would lead to variation of gray level of each perspective image, so that the quality of the 3D image reconstructed on this basis would be affected.

No effective solution has been put forward up till now to solve the problem existing in the prior art on long-time radiation of the target under detection under the X-ray during the process of reconstructing a 3D image by CBCT scanning using a C-arm X-ray machine.

DISCLOSURE OF THE INVENTION

It is a main object of the present invention to provide 3D image generation method and device for a G-arm X-ray machine and a G-arm X-ray machine so as to solve the problem existing in the prior art on long-time radiation of the target under detection under the X-ray during the process of reconstructing a 3D image by CBCT scanning using a C-arm X-ray.

In order to achieve said object, according to one aspect of the invention, a 3D image generation method for a G-arm X-ray machine is provided.

The present invention provides 3D image generation method for a G-arm X-ray machine, comprising: controlling a G-arm frame to rotate to a target angle from an initial angle, obtaining a plurality of groups of 2D projection data of an object under detection when the G-arm is in different angles during the rotation, wherein each group of the 2D projection data comprises two paths of projection data; conducting calculation according to an FDK algorithm or an FDK correction algorithm using the plurality of groups of 2D projection data to obtain a 3D image of the object under detection; outputting the 3D image of the object under detection.

Further, obtaining a plurality of groups of 2D projection data of an object under detection when the G-arm is in different angles during the rotation comprises: setting N image acquiring positions in the range of the initial angle to the target angle; determining the rotation angle of the G-arm frame in real time; when the G-arm frame rotates to the respective image acquiring positions, collecting a group of 2D projection data by means of the two paths of X-ray receivers positioned according to the two paths of X-ray tubes.

Further, angles of every two neighboring image acquiring positions are same.

Further, the angle difference between the initial angle and the target angle is 90°+γ, wherein γ is half angle of X-ray beam emitted by the X-ray tube.

Further, comprising, before controlling the G-arm frame to rotate to a target angle from an initial angle, obtaining setting values of current and voltage of the X-ray tubes;

initiating the two paths of X-ray tubes according to the setting values of current and voltage.

Further, comprising, before controlling, the G-arm frame to rotate to a target angle from an initial angle, measuring spatial distribution of radiation intensities of the X-ray beam radiated by the two paths of X-ray tubes to obtain a function of spatial distribution unevenness; conducting calculation according to an FDK algorithm or an FDK correction algorithm using the plurality of groups of 2D projection data further comprising: calibrating the plurality of groups of 2D projection data using the function of spatial distribution unevenness; conducting calculation according to an FDK algorithm or an FDK correction algorithm using the calibrated 2D projection data.

Further, measuring the spatial distribution of the beam intensities of the X-ray beam emitted by the two paths of X-ray tubes to obtain a function of spatial distribution unevenness comprises: respectively collecting, using the two paths of X-ray receivers, the projection brightness data of the X-ray beams emitted by the two paths of X-ray tubes that have passed through the attenuation plate; using the projection brightness data to respectively calculate the function of spatial distribution unevenness.

Further, comprising, after using the projection brightness data to respectively calculate the function of spatial distribution unevenness of the two paths of X-ray beams: respectively calculating the average radiation intensity of the two paths of X-ray beams, calibrating the plurality of groups of projection data using the function of spatial distribution unevenness comprising: performing a normalization calculation for the plurality of groups of 2D projection data based on the average radiation intensity of the two paths of X-ray beams; calibrating the normalized plurality of groups of 2D projection data using the function of spatial distribution unevenness.

According to another aspect of the invention, a 3D image generation device for a G-arm X-ray machine is provided.

The present invention provides 3D image generation device for a G-arm X-ray machine, characterized in that, comprising: a motion control module for controlling the G-arm to rotate to a target angle from an initial angle; an image data collection module for obtaining a plurality of groups of 2D projection data of the object under detection when the G-arm is in different angles, wherein each group of said 2D projection data includes two paths of projection data; a data processing module for conducting calculation using said plurality of groups of 2D projection data based on an FDK algorithm or an FDK correction algorithm to obtain a 3D image of the object under detection; an outputting module for outputting the 3D image of the object under detection.

Further, the 3D image generation device for a G-arm X-ray machine provided by the present invention further comprises: a ray intensity calibration module for measuring the spatial distribution of the intensities of the X-ray beams emitted by the two paths of X-ray tubes to obtain a function of spatial distribution unevenness.

According to another aspect of the invention, a G-arm X-ray machine is provided, which comprises any 3D image generation device for a G-arm X-ray machine as described above.

According to the technical solution of the invention, the 3D image generation method for a G-arm X-ray machine comprises: controlling a G-arm frame to rotate to a target angle from an initial angle, wherein during the process of rotation, the current and voltage at the two paths of X-ray tubes are kept unchanged; obtaining a plurality of groups of 2D projection data of an object under detection when the G-arm is in different angles during the rotation, wherein each group of the 2D projection data comprises two paths of projection data; conducting calculation according to an FDK algorithm or an FDK correction algorithm using the plurality of groups of 2D projection data to obtain a 3D image of the object under detection; outputting the 3D image of the object under detection. Thus, by obtaining two paths of projection data, the time for obtaining the data is greatly reduced and the radiation time of the object under detection under the X-ray is effectively decreased, and by directly outputting the 3D image of the object under detection, the full view information on the object under detection is reflected.

DESCRIPTION OF THE DRAWINGS

The drawings are provided for further understanding of the invention and constitute a part of the present application. The illustrative examples of interpretations of the invention are used for interpreting the invention but shall not constitute improper limitations on the invention. Among the drawings.

EXEMPLARY EMBODIMENTS

It is to be indicated that without conflict, the examples and the features in the examples in the present application may be combined with each other. The invention is illustrated below in details with reference to the figures and combination with the examples.

Figure 1A:
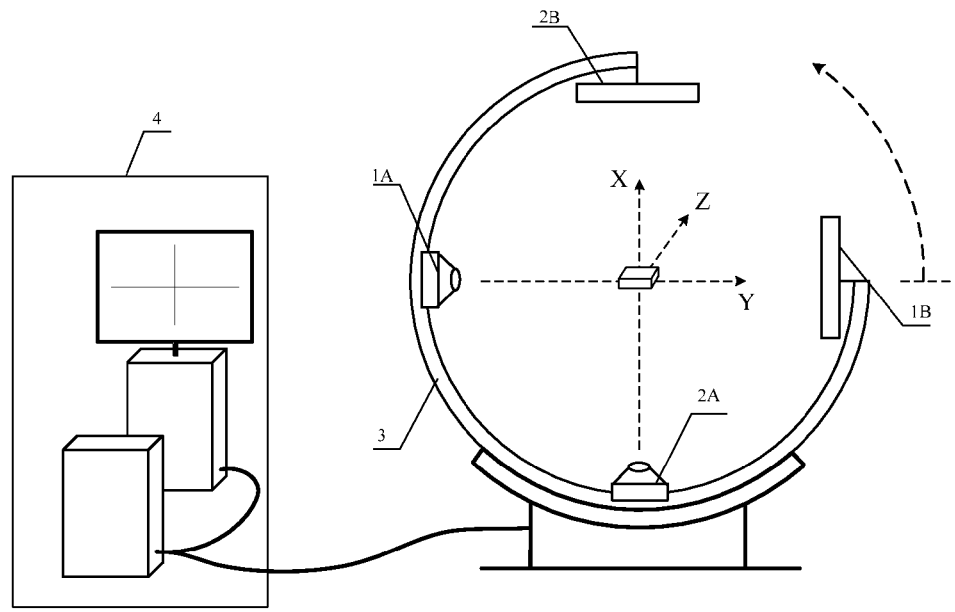
FIG. 1A is a schematic diagram showing that the G-arm frame in the G-arm X-ray machine according to the embodiment of the invention locates in an initial angle.
Figure 1B:
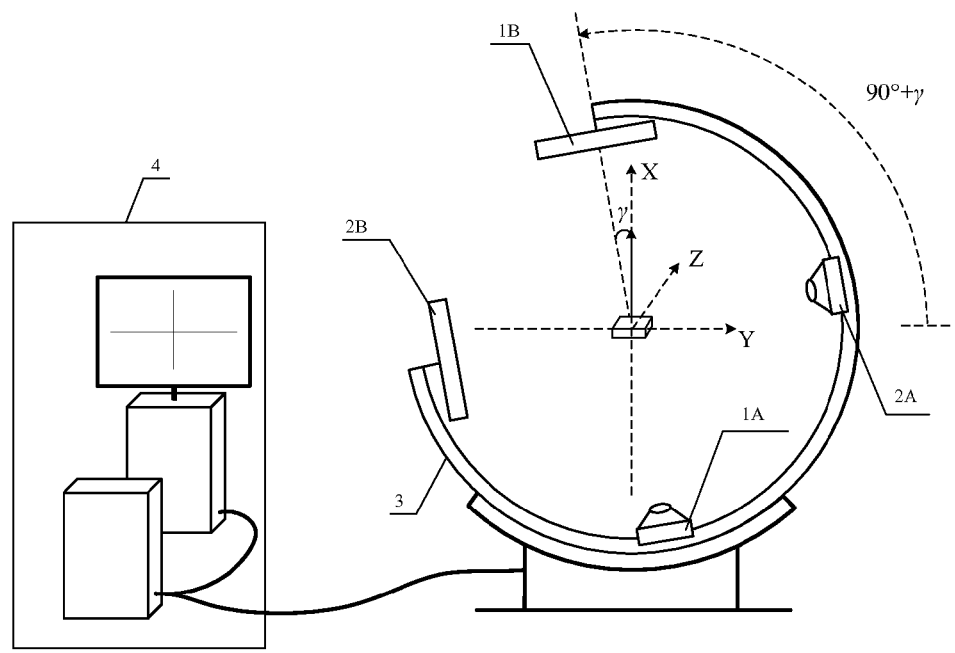
FIG. 1B is a schematic diagram showing that the G-arm frame in the G-arm X-ray machine according to the embodiment of the invention locates in a target angle.

FIGS. 1A and 1B are schematic diagrams showing that in a G-arm X-ray machine according to the embodiment of the invention, the G-arm frame is in an initial angle state and a target angle state. As shown in FIG. 1, different from a single-path X-ray tube of the C-arm, the fixing means for a G-arm X-ray machine is provided with two paths of X-ray tubes 1A and 2A and two paths of X-ray receivers 1B and 2B positioned accordingly. The G-arm frame 3 has a ¾ arc structure. When the G-arm frame 3 is in an initial position, the first X-ray tube 1A is used for emitting lateral cone beam X-rays, and the first X-ray receiver 1B disposed at a position opposite to the first X-ray tube 1A on the G-arm 3 is used for receiving the lateral cone beam X-rays penetrating the object under detection; the second X-ray tube 2A is used for emitting longitudinal cone beam X-rays, and the second X-ray receiver 2B disposed at a position opposite to the second X-ray tube 2A on the G-arm frame 3 is used for receiving longitudinal cone beam X-rays penetrating the object under detection. During the process of scanning the object under detection, the two paths of X-ray tubes 1A and 2A only need to simultaneously rotate counterclockwise or clockwise by 90°+γ, i.e., the G-arm frame 3 rotates from a state of FIG. 1A to a state of FIG. 1B, the 180°+2γ perspective image data of the object under detection can be obtained, which saves half the time for obtaining an image of the C-arm, i.e., the radiation time of the object under detection is reduced by half and the detection efficiency is effectively increased.

The 3D image generation device 4 for the G-arm X-ray machine controls the rotation of the G-arm frame 3 and during the process of rotation, obtains the 2D projection data received by the first X-ray receiver 1B and the second X-ray receiver 2B, and generates a 3D image of the object under detection through calculation based on the 2D projection data in a plurality of directions. The connection line between the first X-ray tube 1A and the first X-ray receiver 1B is perpendicular to the connection line between the second X-ray tube 2A and the second X-ray receiver 2B, and the object under detection is disposed at the center of the arc on which the G-arm 3 locates. The G-arm X-ray machine comprises two paths of X-ray tubes and two paths of X-ray receivers, and a G-arm frame rotatable around the object under detection, so that it is capable of simultaneously collecting projection data of a plurality of orientations in bi-direction, reconstructing the tomography image, reducing the scanning time and increasing the imaging efficiency.

Figure 2:
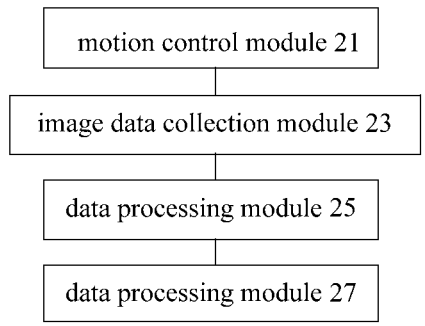
FIG. 2 is a schematic diagram showing the 3D image generation device for the G-arm X-ray machine according to the embodiment of the invention.

FIG. 2 is a schematic diagram showing a 3D image generation device for the G-arm X-ray machine according to the embodiment of the invention. As shown in FIG. 2, the image generation device for the G-arm X-ray machine 3D according to the embodiment of the invention comprises: a motion control module 21 for controlling the G-arm to rotate to a target angle from an initial angle; an image data collection module 23 for obtaining a plurality of groups of 2D projection data of the object under detection when the G-arm 3 is in different angles, wherein each group of said 2D projection data includes two paths of projection data; a data processing module 25 for conducting calculation using said plurality groups of 2D projection data based on an FDK algorithm or an FDK correction algorithm to obtain a 3D image of the object under detection; an outputting module 27 for outputting the 3D image of the object under detection. Said motion control module 21 may be implemented by a control means such as an IPC or a PLC to drive the motor rotating the G-arm frame. Said image data collection data 23 comprises an image collection means for collecting the images received by the X-ray receivers and converting them into a form of digital signals. Said data processing module 25 is implemented by a calculation means with a powerful operational function, such as a computer or a digital signal processor (DSP). Said outputting module may be a display for displaying 3D images, or a memory for storing the 3D image data for use in succeeding analysis.

To obtain full view 3D information on the object under detection, at least it is necessary to perform a 180°+2γ X-ray scanning on the object under detection. In a structure of double-path X-ray scanning of a G-arm X-ray machine according to the embodiment of the invention, it is only necessary to rotate the G-arm frame 3 by 90°+γ to complete the 180°+2γ scanning of the object under detection. Therefore, preferably, the angle difference between the initial angle and the target angle is set to be 90°+γ. Generally speaking, the larger the number of 2D projection images as obtained is, the higher the quality of the 3D image as generated is, but the efficiency of scanning is relatively low and the speed of data processing is relatively slow, so the desired number of 2D projection images may be obtained according to the specific requirements on the generation of the 3D image. Assuming the number of images to be acquired by each path of X-ray receiver is N, the motion control module 21 sets N image acquiring positions in an orientation between the initial angle and the target angle, the rotary angle of the G-arm frame is judged in real-time during the rotation process of the G-arm frame 3; when the G-arm frame rotates to the respective image acquiring positions, the image data collection module 23 collects a group of 2D projection data by means of the two paths of X-ray receivers, so that the N groups of 2D projection images can be obtained during the rotation process.

Preferably, it is ensured that the angles of every two neighboring image acquiring positions are equal to each other. The angles of the initial angle to the target angle are equally divided into N−1 fractions, and the respective positions of equal division points, the initial angle position and the target angle position add up to N image acquiring positions. In other words, per rotation by (90°+γ)/N angle, the two paths of first X-ray receivers 1B and 2B respectively obtain a 2D projection image at this position, and after a rotation by 90°+γ, 2N 2D projection images are obtained.

The intensity of the X-ray needs to be adjusted depending on the type of the object under detection. Therefore, the 3D image generation device for a G-arm X-ray machine according to the embodiment may further comprise an X-ray emission control module for obtaining the setting values of current and voltage at the X-ray tubes 1A and 1B, and initiating the two paths of X-ray tubes 1A and 1B according to the setting values of the current and voltage. During the rotation of the G-arm frame 3, it is ensure that the current value and voltage value of the X-ray tubes are kept constant, so that the intensity of the X-ray is maintained stable to ensure consistency in brightness of the 2D projection images as obtained.

However, due to limitations on the X-ray processing level, it cannot be ensured that the light field intensity of the center ray beam is equal to the light field intensity at other positions, and such inconsistency in light field intensity would lead to variations in gray level of the respective perspective image, so it is necessary to individually mark the light field unevenness for each path of X-rays.

Accordingly, the 3D image generation device for a G-arm X-ray machine according to the embodiment may be further provided with a ray intensity calibration module for measuring the spatial distribution of the radiation intensities of the X-ray beams emitted from the two paths of X-ray tubes 1A and 1B so as to obtain a function of spatial distribution unevenness. The data processing module 25 firstly calibrates the obtained plurality of groups of 2D projection data using the function of spatial distribution unevenness, and then uses the calibrated 2D projection data to conduct calculation according to an FDK algorithm or an FDK correction algorithm. The operating procedure of the ray intensity calibration module is as follows: with two paths of X-ray receivers 1B and 2B, respectively collecting the projection brightness data of the X-rays emitted by the two paths of X-ray tubes 1A and 2A that have passed through the attenuation plate; using the projection brightness data to respectively calculate the function of spatial distribution unevenness of the two paths of X-ray beams.

In addition, the process for manufacturing the X-ray tubes cannot ensure that in case of identical voltage and current, the intensities of the X-rays emitted by all X-ray tubes are completely the same. Therefore, the G-arm has inconsistent intensities of the X-rays emitted from the emission windows of the two paths of X-ray tubes 1A and 2A, which leads to a difference in average brightness of the two paths of perspective images, which is, specifically, one is bright and one is dark. Thus, it is necessary to obtain a relation between the two paths of X-rays in terms of average light field intensity and to perform a normalization process to improve the quality of the 3D image. In this case, the ray intensity calibration module is further used for respectively calculating the average radiation intensity of the two paths of X-rays, and the data processing module 25 conducts a normalization calculation of the plurality of groups of 2D projection data according to the average radiation intensity of the two paths of X-ray beams, and then calibrates the normalized plurality of groups of 2D projection data using the function of spatial distribution unevenness, and uses the calibrated data in the FDK algorithm for calculation.

The plurality of groups of 2D projection data that have been subjected to said processing would ensure the consistency between the images acquired by different X-ray receivers, which would lead to a higher quality of the generated 3D image.

The outputting module 27, besides outputting the 3D image of the object under detection, may also output the XZ section, YZ section and XY section of the object under detection based on the 3D image data obtained from the data processing module 25. Upon outputting, the coordinate of the current position in the three-dimensional target may be output correspondingly to the three sections. Where a display means is used by the output module 27, the entire display area may be divided into four blocks, in which the XZ section, the YZ section, the XY section and the generated 3D image are respectively displayed.

The embodiment of the invention further provides a G-arm X-ray machine, comprising any 3D image generation device for a G-arm X-ray machine as provided by the above content in the embodiment of the invention.

Figure 3:
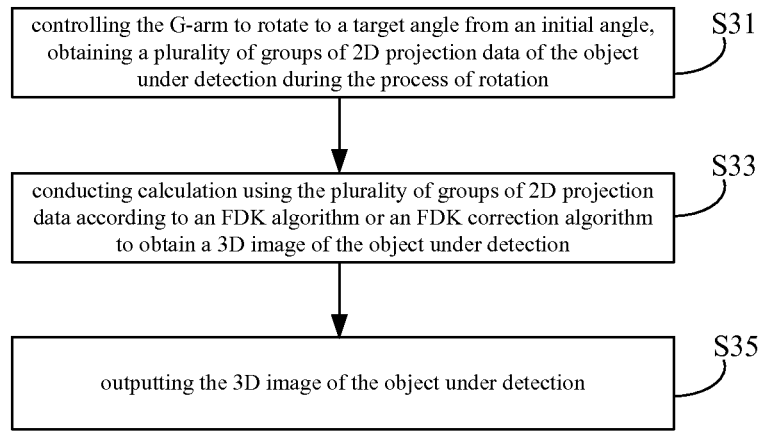
FIG. 3 is a schematic diagram showing the 3D image generation method for the G-arm X-ray machine according to the embodiment of the invention.

The embodiment of the invention further provides a 3D image method for a G-arm X-ray machine, which method can be carried out by any 3D image generation device as provided in the above embodiment of the invention. FIG. 3 is a schematic diagram showing the 3D image method for the G-arm X-ray machine. As shown in FIG. 3, the 3D image generation method for a G-arm X-ray machine according to the embodiment of the invention comprises:

Step S31, controlling the G-arm frame to rotate to a target angle from an initial angle, during the process of the rotation, acquiring a plurality of groups of 2D projection data of the object under detection when the G-arm is indifferent angles, wherein each group of 2D projection data comprises two paths of projection data.

Step S33, conducting calculation using the plurality of groups of 2D projection data according to an FDK algorithm or an FDK correction algorithm to obtain a 3D image of the object under detection.

Step S35, outputting the 3D image of the object under detection.

The desired number of 2D projection images may be obtained according to the specific requirements on the generation of the 3D image. Assuming the number of images to be acquired by each path of X-ray receiver is N, the obtaining of a plurality of groups of 2D projection data of the object under detection when the G-arm is in different angles during the rotation in step S31 may comprise: setting N image acquiring positions in a range between the initial angle and the target angle, judging in real-time the rotary angle of the G-arm frame; when the G-arm frame rotates to the respective image acquiring positions, collecting a group of 2D projection data by means of the two paths of X-ray receivers disposed according to the two paths of X-ray tubes.

Angles of every two neighboring image acquiring positions may be set to be equal to each other, by equally dividing the angles between the initial angle and the target angle into N−1 fractions, wherein the respective positions of equal division points, the initial angle position and the target angle position add up to N image acquiring positions.

To obtain full view 3D information on the object under detection, at least it is necessary to perform a 180°+2γ X-ray scanning on the object under detection. In a structure of double-path X-ray scanning of the G-arm X-ray machine according to the embodiment of the invention, it is only necessary to rotate the G-arm frame 3 by 90°+γ to complete the 180°+2γ scanning of the object under detection. Therefore, preferably, the angle difference between the initial angle and the target angle may be set to be 90°+γ. At this time, determining the image acquiring position according to the equally dividing manner would ensure per rotation by (90°+γ)/N angle, the two paths of first X-ray receivers 1B and 2B respectively acquire a 2D projection image at this position, and after a rotation by 90°+γ, 2N 2D projection images are obtained.

In order to ensure the intensity of the X-ray meets the requirement on the scanning of the object under detection, further comprising, before controlling the G-arm frame to rotate from an initial angle to a target angle: obtaining setting values of current and voltage at the X-ray tubes, and initiating the two paths of X-ray tubes according to the setting values of the current and voltage. During the rotation of the G-arm frame 3, it is ensure that the current value and voltage value of the X-ray tubes are kept constant, so that the intensity of the X-ray is maintained stable. The setting values of current and voltage of said X-ray tubes vary depending on the type of the object under detection and can be flexibly set.

Due to limitations on the X-ray processing level, it cannot be ensured that the light field intensity of the center ray beam is equal to the light field intensity at other positions, and such inconsistency in light field intensity would lead to variations in gray level of the respective perspective images, so it is necessary to individually mark the light field unevenness for each path of X-rays. The specific marking procedure is as follows: before controlling the G-arm to rotate to a target angle from an initial angle, further comprising: measuring the spatial distribution of the radiation intensities of the X-ray beams emitted from the two paths of X-ray tubes to obtain a function of spatial distribution unevenness. Then, in said step S31, conducting calculation using the plurality of groups of 2D projection data according to an FDK algorithm or an FDK correction algorithm comprises: calibrating the plurality of groups of 2D projection data using the function of spatial distribution unevenness; using the calibrated 2D projection data to conduct calculation according to an FDK algorithm or an FDK correction algorithm.

The specific procedure of measuring the spatial distribution of the intensities of X-ray beams emitted from the two paths of X-ray tubes to obtain a function of spatial distribution unevenness is as follows: with two paths of X-ray receivers, respectively collecting the projection brightness data of the X-rays emitted by the two paths of X-ray tubes that have passed through the attenuation plate; using the projection brightness data to respectively calculate the function of spatial distribution unevenness of the two paths of X-ray beams. The method for testing the X-ray spatial unevenness is introduced based on the figures as follows.

Figure 4:
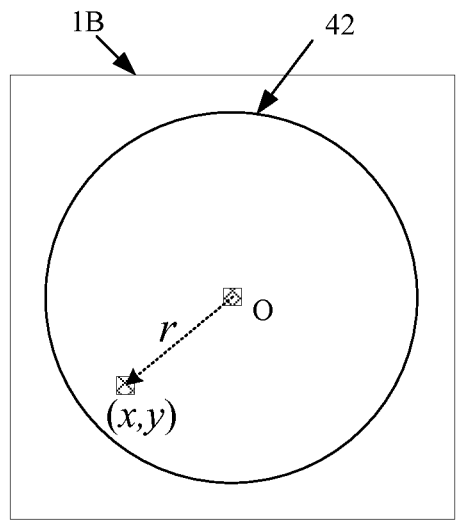
FIG. 4 is a schematic diagram showing the projection of the cone beam X-ray on the X-ray receiver in the 3D image generation method for the G-arm X-ray machine according to the embodiment of the invention.
Figure 5A:
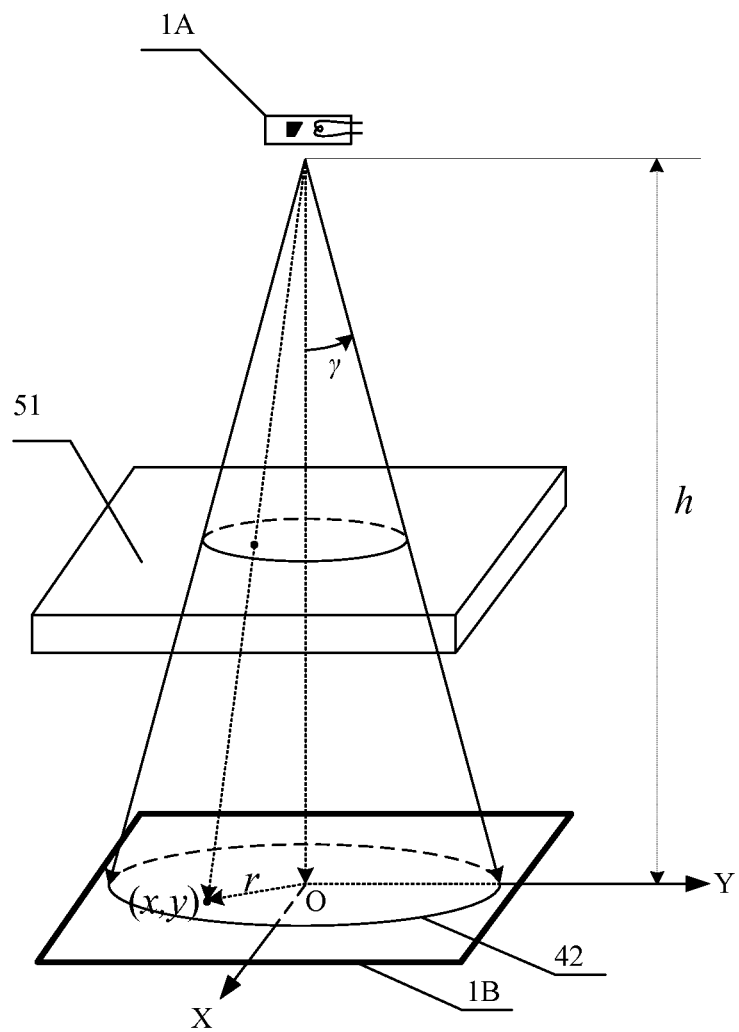
FIG. 5A is a stereoscopic diagram showing X-ray spatial distribution unevenness in the 3D image generation method for the G-arm X-ray machine according to the embodiment of the invention.
Figure 5B:
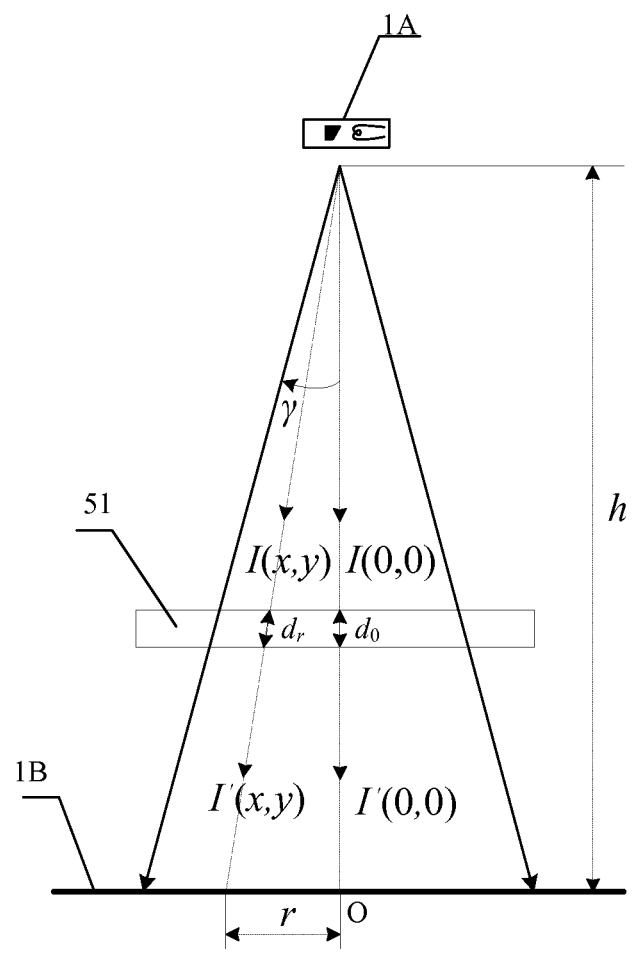
FIG. 5B is a planar diagram showing X-ray spatial distribution unevenness in the 3D image generation method for the G-arm X-ray machine according to the embodiment of the invention.

FIG. 4 is a schematic diagram showing the projection of the cone beam X-ray on the X-ray receiver in the 3D image generation method for a G-arm X-ray machine according to the embodiment of the invention; FIG. 5A is a stereoscopic diagram showing the X-ray spatial distribution unevenness in the 3D image generation method for a G-arm X-ray machine according to the embodiment of the invention, FIG. 5B is a planar diagram showing the X-ray spatial distribution unevenness in the 3D image generation method for a G-arm X-ray machine according to the embodiment of the invention. In the figures, the first X-ray tube 1A and the first X-ray receiver 1B are taken as examples, but the spatial distribution of the second X-ray tube 2A and the second X-ray receiver 2B is measured in the same manner.

In said figures, 42 is a projection range of the cone-shape X-ray beam on the X-ray receiver 1B, point O is the projection position of the center beam of the cone beam X-ray on the X-ray receiver 1B, the point (x, y) is a projection position of the beam 2 on the X-ray receiver 1B, the angle between the beam 2 and the center beam is θ, the distance from the point O to the point (x, y) is r, 51 is an attenuation plate with a uniform texture, the distance between the first X-ray tube 1A and the first X-ray receiver 1B is h, and $d_r$, $d_0$ are respectively the distances of the beam 2 and the center beam penetrating the attenuation plate 51.

The first X-ray tube 1A has an uneven distribution of X-ray radiation intensities under different voltage values (kV), which varies with the spatial position. Assuming the intensity of the center beam is $I_0$, the intensity of the beam at the point (x, y) is I, as shown in FIG. 5. The uneven distribution of the intensities of the X-rays emitted by the X-ray tubes may be obtained by measuring the image data received by the receivers. The specific method comprises: placing an attenuation plate 51 with a uniform texture between the first X-ray tube and the first X-ray receiver 1B perpendicular to the center beam, measuring the light field intensity data $I_{x,y}$ received by the X-ray receiver, as shown in FIG. 5, and filtering the light field intensity data $I_{x,y}$ received by the X-ray receiver by a filter, followed by a smoothing process to obtain processed light field intensity data $I_{(x,y)}$.

After a single-energy X-ray having an intensity of I penetrates the uniformly structured attenuation plate, the attenuation of the ray beam shall comply with the Beer Rule. Considering the angle relation o between the center beam and the beam 2, as well as the length $d_r$, $d_0$ relation of the path the beam penetrates the attenuation plate, the unevenness ρ (x, y, kV) of the light intensity of the light emitted from the X-ray tube under a certain kV voltage in the coordinate (x, y) is calculated as follows:

$$\rho(x, y, \text{kV}) =$$

-continued $$\frac{I(x, y, \text{kV})}{I(0, 0, \text{kV})} = \frac{I'(x, y, \text{kV})}{I'(0, 0, \text{kV})} \exp\left[\mu(\text{kV}) \times \left(\frac{\sqrt{x^2 + y^2 + h^2}}{h} - 1\right) d_0\right]$$

wherein μ is an X-ray attenuation coefficient of the attenuation plate 51 under the test voltage, and $d_0$ is the thickness of the attenuation plate. It is seen that the X-ray outgoing light field intensity ρ of the X-ray tube is a function of the position (x, y) as well as a function that varies with the voltage. The function of spatial distribution unevenness of the second X-ray tube may be measured by the same method.

ρ (x, y, kV) is made into a three-dimensional matrix, in which the first two dimensions are the values of the coordinate (x, y), while the third dimension is the test voltage value. By gradually changing the intensity of the voltage, a series of accurate data of the outgoing light intensity unevenness varying with the voltage may be obtained, and the data between two voltage changes may be determined by means of interpolation. Hence, the function of spatial distribution unevenness is obtained. In said step S31, when conducting calculation using the plurality of groups of 2D projection data according to an FDK algorithm or an FDK correction algorithm, it is necessary to first calibrate the plurality of groups of 2D projection data using the function of spatial distribution unevenness to eliminate the influence of the spatial distribution on the data of all the points in the 2D image, and then the calibrated 2D projection data are used for the calculation according to an FDK algorithm or an FDK correction algorithm.

In addition, the process for manufacturing the X-ray tubes cannot ensure that in case of identical voltage and current, the intensities of the X-rays emitted by all X-ray tubes are completely the same. Therefore, the G-arm has inconsistent intensities of the X-rays emitted from the emission windows of the two paths of X-ray tubes 1A and 2A, which leads to a difference in average brightness of the two paths of perspective images, which is, specifically, one is bright and one is dark. Thus, it is necessary to obtain a relation between the two paths of X-rays in terms of average light field intensity and to perform a normalization process so as to improve the quality of the generated 3D image.

Figure 6:
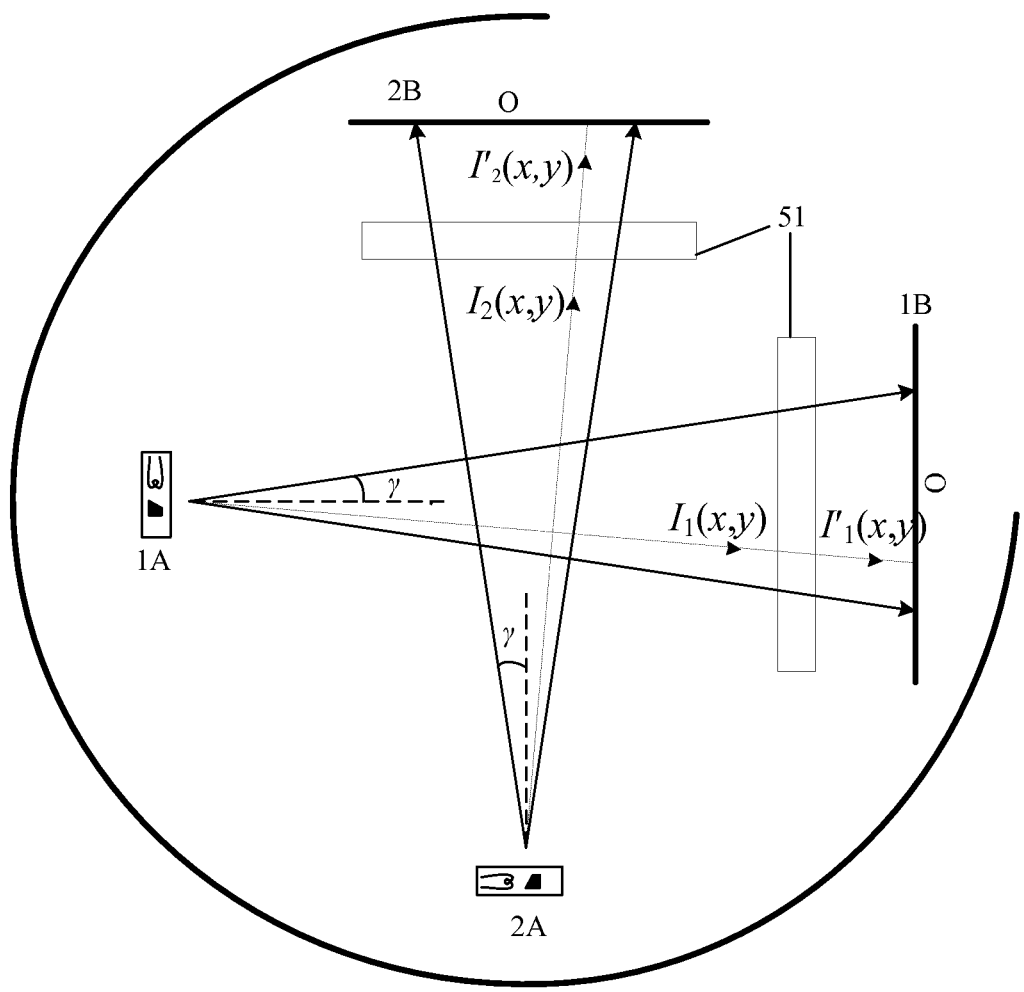
FIG. 6 is a schematic diagram showing the test of inconsistency between the two paths of X-rays in the 3D image generation method for the G-arm X-ray machine according to the embodiment of the invention.

FIG. 6 is a schematic diagram showing the test on the inconsistency between the two paths of X-rays in 3D image generation method for the G-arm X-ray according to the embodiment of the invention. Generally, due to limitations on the process for manufacturing the X-ray tubes, it cannot be ensured that the two paths of X-ray tubes are completely the same. Thus, even if the same input signal is set, in addition to unevenness, the X-ray radiation intensities of the two paths of X-ray tubes have different average radiation intensities. Therefore, it is also necessary to determine the degree of inconsistency between the radiation intensities of the two paths of X-rays and to eliminate such a degree of inconsistency by compensation. As shown in FIG. 6, under the same input conditions, the same attenuation plate 51 is respectively placed between the two paths of X-ray emission sources and X-ray receivers, perpendicular to the X-ray beam, the light field intensity data received by the X-ray receivers are measured, and the light field intensity data are filtered to respectively obtain average radiation data $I'_{1(x, y)}$ for the first path of X-rays and radiation data $I'_{2(x, y)}$ for the second path of X-rays.

Based on the Beer Rule and the formula of unevenness, resolving the incident light field intensity I(x, y, kV), and based on the following formula, calculating the average radiation data $I_{ave}$ for each path:

$$I_{ave}(kV) = \frac{1}{2\pi(1-\cos\gamma)}\int_\Omega I(x, y, kV) d\Omega,$$

wherein $\gamma$ is the half angle of the cone beam X-ray, and $\Omega$ is the curvature integration space.

Accordingly, by using the method, the average radiation intensity data $I_{ave1}(kV)$ for the first path of X-rays and the average radiation intensity data $I_{ave2}(kV)$ for the second path of X-rays can be obtained. Having $$\eta(kV) = \frac{I_{ave2}(kV)}{I_{ave1}(kV)},$$

the relation between the average radiation intensities of the two paths of X-rays would be obtained. Thus, using $\eta(kV)$, the double-path X-ray beam projections can be normalized as projections under $I_{ave1}(kV)$ alone.

Thus, the 3D image generation method for a G-arm X-ray according to the embodiment of the invention may further comprise, after using the projection brightness data to respectively calculate the function of spatial distribution unevenness of the two paths of X-ray beams: respectively calculating the average radiation intensities of the two paths of X-ray beams, and using the function of spatial distribution unevenness to calibrate the plurality of groups of 2D projection data comprises: performing a normalization calculation on the plurality of groups of 2D projection data according to the average radiation intensities of the two paths of X-ray beams; and using the function of spatial distribution unevenness to calibrate the normalized plurality of groups of 2D projection data.

According to the technical solution of the invention, the 3D image generation method for a G-arm X-ray machine comprises: controlling the G-arm frame to rotate to a target angle from an initial angle, wherein the current and voltage of the two paths of X-ray tubes are kept unchanged during the rotation; acquiring a plurality of groups of 2D projection data of the object under detection when the G-arm is in different angles, wherein each group of the 2D projection data comprises two paths of projection data; conducting calculation according to an FDK algorithm or an FDK correction algorithm using the plurality of groups of 2D projection data to obtain a 3D image of the object under detection; outputting the 3D image of the object under detection. Thus, by obtaining two paths of projection data, the time for obtaining the data is greatly reduced and the radiation time of the object under detection under the X-ray is effectively decreased, and by directly outputting the 3D image of the object under detection, the full view information on the object under detection is reflected.

Apparently, it shall be understood by those skilled in the art that the respective modules or steps of the invention as described above may be implemented by a general computing means; they may be integrated on a single computing means or distributed on a network consisting of a plurality of computing means; optionally, they may be implemented by program codes executable by a computing means, so that they may be stored in a storage means and be performed by a computing means, or they may be individually made into respective integrated circuit modules, or a plurality of modules or steps thereof may be made into a single integrated circuit module. Hence, the present invention is not limited to any special combination of hardware with software.

The above are only preferred examples for the invention, but shall by no means limit the invention. For those skilled in the art, the invention may have various modifications and variations. As long as within the spirits and rules of the invention, any amendment, equivalent replacement, improvement, etc., shall be included in the extent of protection sought for in the invention.

The invention claimed is:

1. A 3D image generation method for a G-arm X-ray machine, characterized in that, comprising,
controlling a G-arm frame to rotate to a target angle from an initial angle, obtaining a plurality of groups of 2D projection data of an object under detection when the G-arm is in different angles during the rotation, wherein each group of the 2D projection data comprises two paths of projection data;
conducting calculation according to an FDK algorithm or an FDK correction algorithm using the plurality of groups of 2D projection data to obtain a 3D image of the object under detection; and
outputting the 3D image of the object under detection;
characterized in that, obtaining a plurality of groups of 2D projection data of an object under detection when the G-arm is in different angles during the rotation comprises:
setting N image acquiring positions in the range of the initial angle to the target angle;
determining rotation angle of the G-arm frame in real time; and
when the G-arm frame rotates to the respective image acquiring positions, collecting a group of 2D projection data by means of the two paths of X-ray receivers positioned according to the two paths of X-ray tubes.

2. The 3D image generation method according to claim 1, characterized in that, angles of every two neighboring image acquiring positions are same.

3. The 3D image generation method according to claim 2, characterized in that, further comprising, before controlling the G-arm frame to rotate to a target angle from an initial angle:
measuring spatial distribution of radiation intensities of the X-ray beams emitted by the two paths of X-ray tubes to obtain a function of spatial distribution unevenness;
conducting calculation according to an FDK algorithm or an FDK correction algorithm using the plurality of groups of 2D projection data comprising:
calibrating the plurality of groups of 2D projection data using the function of spatial distribution unevenness; and
conducting calculation according to an FDK algorithm or an FDK correction algorithm using the calibrated 2D projection data.

4. The 3D image generation method according to claim 1, characterized in that, the angle difference between the initial angle and the target angle is 90°+$\gamma$, wherein $\gamma$ is half angle of the X-ray beam emitted by the X-ray tube.

5. The 3D image generation method according to claim 4, characterized in that, further comprising, before controlling the G-arm frame to rotate to a target angle from an initial angle:
measuring spatial distribution of radiation intensities of the X-ray beams emitted by the two paths of X-ray tubes to obtain a function of spatial distribution unevenness;

conducting calculation according to an FDK algorithm or an FDK correction algorithm using the plurality of groups of 2D projection data comprising:
  calibrating the plurality of groups of 2D projection data using the function of spatial distribution unevenness; and
  conducting calculation according to an FDK algorithm or an FDK correction algorithm using the calibrated 2D projection data.

6. The 3D image generation method according to claim 1, characterized in that, further comprising, before controlling the G-arm to rotate to a target angle from an initial angle:
  obtaining setting values of current and voltage of the X-ray tubes; and
  initiating the two paths of X-ray tubes according to the setting values of current and voltage.

7. The 3D image generation method according to claim 6, characterized in that, further comprising, before controlling the G-arm frame to rotate to a target angle from an initial angle:
  measuring spatial distribution of radiation intensities of the X-ray beams emitted by the two paths of X-ray tubes to obtain a function of spatial distribution unevenness;
  conducting calculation according to an FDK algorithm or an FDK correction algorithm using the plurality of groups of 2D projection data comprising:
  calibrating the plurality of groups of 2D projection data using the function of spatial distribution unevenness; and
  conducting calculation according to an FDK algorithm or an FDK correction algorithm using the calibrated 2D projection data.

8. The 3D image generation method according to claim 1, characterized in that, further comprising, before controlling the G-arm frame to rotate to a target angle from an initial angle:
  measuring spatial distribution of radiation intensities of the X-ray beams emitted by the two paths of X-ray tubes to obtain a function of spatial distribution unevenness;
  conducting calculation according to an FDK algorithm or an FDK correction algorithm using the plurality of groups of 2D projection data comprising:
  calibrating the plurality of groups of 2D projection data using the function of spatial distribution unevenness; and
  conducting calculation according to an FDK algorithm or an FDK correction algorithm using the calibrated 2D projection data.

9. The 3D image generation method according to claim 8, characterized in that, measuring spatial distribution of radiation intensities of the X-ray beams emitted by the two paths of X-ray tubes to obtain a function of spatial distribution unevenness comprises:
  respectively collecting, using the two paths of X-ray receivers, the projection brightness data of the X-ray beams emitted by the two paths of X-ray tubes that have passed through the attenuation plate; and
  using the projection brightness data to respectively calculate the function of spatial distribution unevenness for said two paths of X-ray beams.

10. The 3D image generation method according to claim 9, characterized in that,
  further comprising, after using the projection brightness data to respectively calculate the function of spatial distribution unevenness for said two paths of X-ray beams: respectively calculating the average radiation intensity of the two paths of X-ray beams,
  calibrating the plurality of groups of 2D projection data using the function of spatial distribution unevenness comprising:
  performing normalization calculation for the plurality of groups of 2D projection data based on the average radiation intensities of the two paths of X-ray beams; and
  calibrating the normalized plurality of groups of 2D projection data using the function of spatial distribution unevenness.

11. The 3D image generation method according to claim 1, characterized in that, further comprising, before controlling the G-arm frame to rotate to a target angle from an initial angle:
  measuring spatial distribution of radiation intensities of the X-ray beams emitted by the two paths of X-ray tubes to obtain a function of spatial distribution unevenness;
  conducting calculation according to an FDK algorithm or an FDK correction algorithm using the plurality of groups of 2D projection data comprising:
  calibrating the plurality of groups of 2D projection data using the function of spatial distribution unevenness; and
  conducting calculation according to an FDK algorithm or an FDK correction algorithm using the calibrated 2D projection data.

12. A 3D image generation device for a G-arm X-ray machine, characterized in that, comprising:
  a motion control module for controlling the G-arm to rotate to a target angle from an initial angle;
  an image data collection module for obtaining a plurality of groups of 2D projection data of the object under detection when the G-arm is in different angles, wherein each group of said 2D projection data includes two paths of projection data;
  a data processing module for conducting calculation using said plurality of groups of 2D projection data based on an FDK algorithm or an FDK correction algorithm to obtain a 3D image of the object under detection;
  an outputting module for outputting the 3D image of the object under detection; and
  a ray intensity calibration module for measuring the spatial distribution of the intensities of the X-ray beams emitted by the two paths of X-ray tubes to obtain a function of spatial distribution unevenness.

13. A G-arm X-ray machine, characterized in that, comprising the 3D image generation device of claim 12.

* * * * *